(12) United States Patent
Whinnery et al.

(10) Patent No.: US 11,865,235 B2
(45) Date of Patent: Jan. 9, 2024

(54) VEHICLE CABIN DISINFECTION SYSTEMS AND METHODS

(71) Applicant: Lyft, Inc., San Francisco, CA (US)

(72) Inventors: Joseph Patrick Wendell Whinnery, Soquel, CA (US); Azhar Kamal Meyer, Pacifica, CA (US); Benjamin Patrick Rhoads, Palo Alto, CA (US)

(73) Assignee: Lyft, Inc., San Francisco, CA (US)

( * ) Notice: Subject to any disclaimer, the term of this patent is extended or adjusted under 35 U.S.C. 154(b) by 659 days.

(21) Appl. No.: 16/915,791

(22) Filed: Jun. 29, 2020

(65) Prior Publication Data

US 2021/0402041 A1 Dec. 30, 2021

(51) Int. Cl.
*A61L 9/20* (2006.01)
*A61L 2/24* (2006.01)
*A61L 2/10* (2006.01)

(52) U.S. Cl.
CPC ....... *A61L 9/20* (2013.01); *A61L 2/10* (2013.01); *A61L 2/24* (2013.01); *A61L 2202/11* (2013.01); *A61L 2202/14* (2013.01); *A61L 2202/25* (2013.01); *A61L 2209/111* (2013.01); *A61L 2209/12* (2013.01); *A61L 2209/16* (2013.01)

(58) Field of Classification Search
None
See application file for complete search history.

(56) References Cited

U.S. PATENT DOCUMENTS 6,787,782 B1 * 9/2004 Krosney .............. A61L 9/20
250/435
2019/0030195 A1 * 1/2019 Hatti .................. A61L 2/24

* cited by examiner

*Primary Examiner* — Andrew Smyth
(74) *Attorney, Agent, or Firm* — Baker Botts L.L.P.

(57) ABSTRACT

Systems and methods are provided for disinfecting a cabin of a vehicle. In one example, a disinfection system comprises a controller, an ultraviolet radiation source, an air duct, and a steerable optical system. The ultraviolet radiation source is in communication with the controller, disposed within the air duct, and configured to emit ultraviolet radiation. The air duct comprises an inlet configured to receive air particles from within the cabin. The air duct comprises one or more internal reflective surfaces configured to reflect the ultraviolet radiation so as to disinfect the air particles within the air duct. The air duct comprises an outlet configured to transmit the disinfected air particles out of the air duct via the outlet. The steerable optical system is coupled to the air duct and configured to receive and selectively direct the ultraviolet radiation to disinfect the cabin. Additional systems and related methods are provided.

20 Claims, 9 Drawing Sheets

VEHICLE CABIN DISINFECTION SYSTEMS AND METHODS

TECHNICAL FIELD

One or more embodiments of the present disclosure relate generally to vehicles and more particularly, for example, to systems and methods for disinfecting a cabin of a vehicle.

BACKGROUND

In the field of transportation, various systems have been used to disinfect vehicle cabins to remove potential contaminants. In the case of airborne contaminants, conventional filtration systems may rely on physical media filters. For example, vehicle Heating Ventilation and Air Conditioning (HVAC) systems may include physical media filters to capture airborne contaminants before they enter the cabin or as the air is recirculated. Although such systems can be helpful in removing certain contaminants, their effectiveness can be compromised by the size limitations of the physical media filters and the need to periodically clean or replace the filters.

In the case of surface-based contaminants, conventional disinfection techniques typically rely on physical cleaning of cabin surfaces through manual labor. While such techniques can be effective, they are nevertheless subject to certain limitations. For example, a person engaging in manual disinfection efforts may not necessarily be aware of which areas in the cabin have been physically touched by a previous occupant. Moreover, the effectiveness of such techniques are dependent on the thoroughness of the person performing the disinfection.

Accordingly, there is a need for an improved approach to vehicle cabin disinfection that overcomes the deficiencies of physical media filters and manual disinfection efforts, other deficiencies known in the industry, or at least offers a useful alternative to current techniques.

SUMMARY

Systems and methods are provided for disinfecting a cabin of a vehicle. In one embodiment, a disinfection system comprises a controller, an ultraviolet radiation source, an air duct, and a steerable optical system. The ultraviolet radiation source is in communication with the controller, disposed within the air duct, and configured to emit ultraviolet radiation. The air duct comprises an inlet configured to receive air particles from within the cabin. The air duct comprises one or more internal reflective surfaces configured to reflect the ultraviolet radiation so as to disinfect the air particles within the air duct. The air duct comprises an outlet configured to transmit the disinfected air particles out of the air duct via the outlet. The steerable optical system is coupled to the air duct and configured to receive and selectively direct the ultraviolet radiation to disinfect the cabin. Additional systems and related methods are provided.

In another embodiment, a method of performing a disinfection process for a cabin of a vehicle by a controller is provided, wherein the cabin includes an air duct. The method comprises receiving, from a sensor in communication with the controller, an indication of one or more surfaces of the cabin that are to undergo the disinfection process. The method also comprises adjusting an orientation of a steerable optical system coupled to the air duct based on the indication of the one or more surfaces of the cabin that are to undergo the disinfection process. The method further comprises, while the steerable optical system is in the orientation, causing an ultraviolet radiation source in communication with the controller to direct ultraviolet radiation to the steerable optical system. The ultraviolet radiation source is disposed within the air duct, and the air duct includes one or more internal reflective surfaces that reflect the ultraviolet radiation towards the steerable optical system such that the steerable optical system selectively directs the ultraviolet radiation to the one or more surfaces of the cabin.

In another embodiment, a disinfection system for a cabin of a vehicle comprises a controller, an ultraviolet radiation source, an air duct, a sensor, and a steerable optical system. The ultraviolet radiation source is in communication with the controller and configured to emit ultraviolet radiation. The air duct is defined by an inlet and an outlet, the ultraviolet radiation source disposed within the air duct, wherein the air duct includes one or more internal reflective surfaces configured to reflect the ultraviolet radiation emitted by the ultraviolet radiation source. The sensor is in communication with the controller, the sensor configured to (i) determine a presence of a disinfection event in the cabin, and (ii) provide an indication to the controller of one or more surfaces of the cabin that are to be disinfected in association with the disinfection event. The steerable optical system includes one or more optical elements coupled to the air duct, the one or more optical elements configured to transition between a first shape and a second shape, the steerable optical system configured to (i) transition from the first shape to the second shape, and (ii) receive the ultraviolet radiation and selectively direct the ultraviolet radiation by the one or more optical elements while in the second shape to disinfect the one or more surfaces of the cabin.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Figure 1:
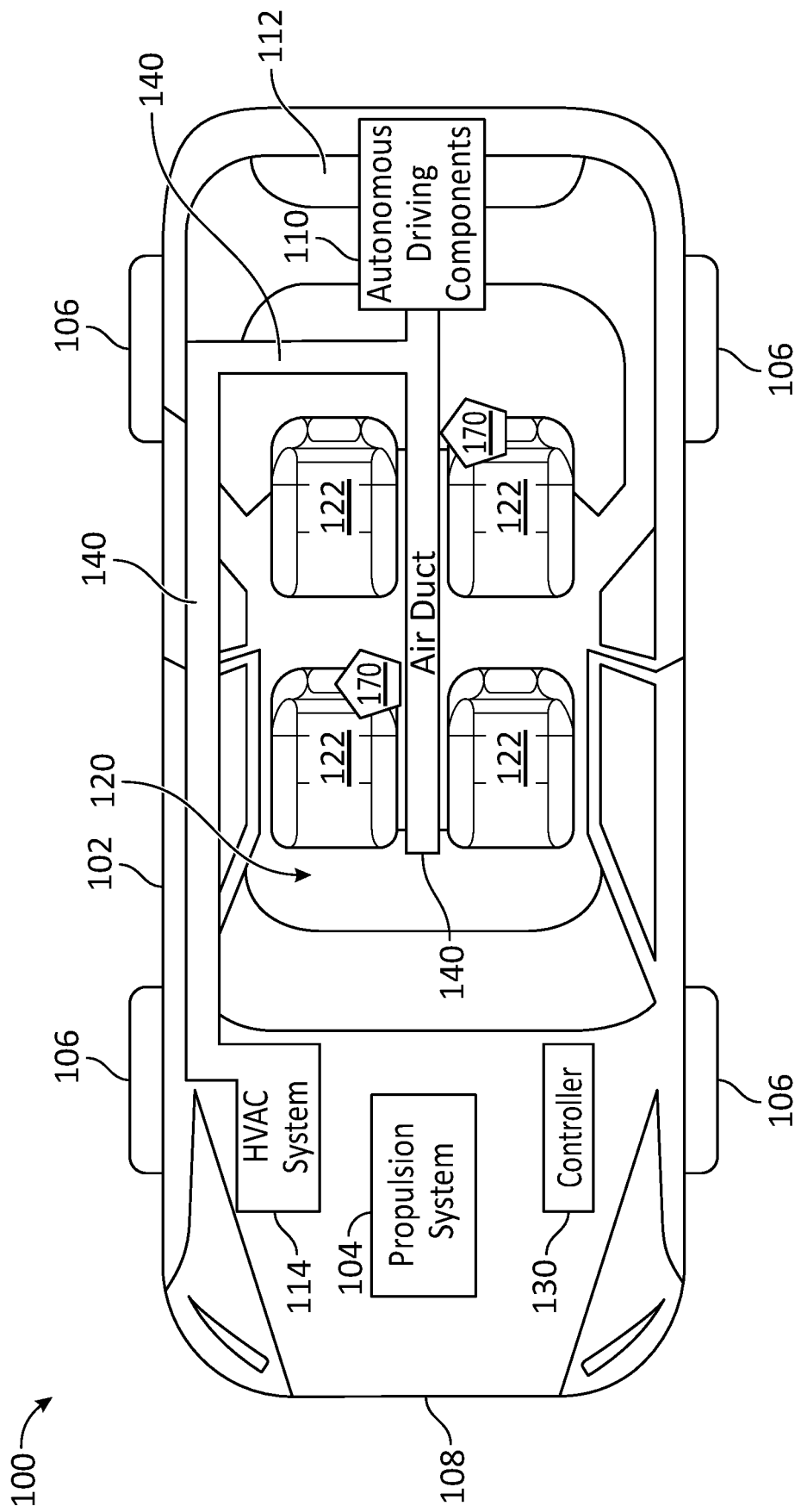
FIG. 1 illustrates a block diagram of a vehicle with components of a cabin disinfection system in accordance with an embodiment of the disclosure.

In accordance with embodiments disclosed herein, systems and methods are provided for implementing and operating a cabin disinfection system for a vehicle. In particular, the disclosed embodiments provide improved approaches for disinfecting (e.g., decontaminating) vehicle cabins in an efficient manner to neutralize airborne and surface-based contaminants. Such techniques are especially useful in the context of rideshare vehicles where many different persons may occupy a vehicle cabin in a short period of time.

In accordance with various embodiments, an air duct is provided with an ultraviolet radiation source disposed therein. Air particles are drawn from a vehicle cabin into the air duct through one or more inlets. The air duct may be implemented with internal reflective surfaces such that ultraviolet radiation provided by the ultraviolet radiation source is reflected within the air duct, thereby causing the air duct to operate as a reflective waveguide to efficiently disperse the ultraviolet radiation to the air particles passing through the air duct. As a result, possible contaminants carried by the air particles may be neutralized, thus effectively disinfecting the air particles. In various embodiments, the air duct may be positioned in a headliner, floor, side panels, and/or elsewhere in a vehicle cabin to neutralize different types of contaminants.

In some embodiments, the air duct may be integrated with a forced air system which may be used to draw the air particles through the air duct. In some embodiments, the forced air system may be a cooling system used for cooling one or more autonomous driving components. Such an implementation can facilitate efficient implementations of the cabin disinfection system, as a forced air system used for cooling the autonomous driving components may also be used to propel the air particles through the air duct of the disinfection system.

In addition, by drawing air particles from the air duct, the disinfected air particles ultimately received by the forced air system may originate from areas deep inside the vehicle cabin (e.g., up to several feet away). Advantageously, such air particles may be at lower temperatures than those in proximity to the autonomous driving components. As a result, the disinfected air particles applied to cool the autonomous driving components may provide improved cooling over conventional air cooling implementations.

In addition to the radiation applied within the reflective waveguide of the air duct, radiation may also be applied directly to the vehicle cabin for neutralizing surface-based contaminants. In some embodiments, the radiation may be directed through the use of one or more steerable optical systems providing optical elements having various shapes. The optical elements may be implemented as reflectors, lenses, and/or other types of optical elements as appropriate.

For ease of illustration and visual clarity for the reader, various steerable reflector systems having optical elements implemented by reflectors are further described herein. However, it will be appreciated that steerable lens systems having optical elements implemented by lenses and/or combinations of steerable reflector systems and steerable lens systems may be used in accordance with the principles of the present disclosure.

In the case of optical elements implemented by reflectors, for example, a concave reflector shape may be used to provide a high intensity concentrated radiation beam profile to focus the radiation on surfaces having a significant likelihood of contamination, such as high touch surfaces commonly contacted by occupants of the vehicle cabin. Conversely, a convex reflector shape may be used to provide low intensity diffused radiation beam profile to exhibit a generalized distribution of low intensity radiation throughout the vehicle cabin. In the case of optical elements implemented by lenses, for example, a convex lens shape may be used to provide the high intensity concentrated radiation beam profile, and a concave lens shape may be used to provide the low intensity diffused radiation beam profile.

Sensors may detect the presence of occupants to determine the timing, intensity, and locations for radiation applied to the vehicle cabin. For example, high intensity radiation may be applied to high contact surfaces of the cabin when no occupants are detected. Conversely, low intensity radiation applied at a safe dosage and/or for a safe duration of time or no radiation may be applied when occupants are detected. Various radiation intensities may be used. For example, in some embodiments, radiation intensities ranging between 0 and 30 microwatts per square centimeter ($\mu$W cm-2) may be used. Other intensity ranges may be used in other embodiments as appropriate.

The various features disclosed herein may be implemented in a multitude of different vehicle types having enclosed cabins such as cars, trucks, sport utility vehicles, vans, airplanes, trains, and other vehicles as appropriate. The disclosed features are particularly useful in rideshare vehicles where many different occupants may transition in and out of the vehicle cabin in a relatively short period of time. By providing vehicle disinfection systems and methods of the types disclosed herein, rideshare vehicles may be efficiently disinfected and maintained in a clean and acceptable condition for repeated use. These and other aspects of the disclosure will be further understood with reference to the following discussion of the various figures.

FIG. 1 illustrates a block diagram of a vehicle 100 with components of a cabin disinfection system in accordance with an embodiment of the disclosure. Although various components of vehicle 100 are illustrated as residing in particular locations, it will be understood that this is only for purposes of example and that any of the illustrated components may be positioned in other locations, added to, and/or omitted as appropriate depending on the type of vehicle 100. For example, although vehicle 100 is illustrated as a car, it will be appreciated that other types of vehicles may be provided as discussed.

As shown, vehicle 100 includes a body 102 that defines a front compartment 106 (e.g., engine compartment), a rear compartment 112 (e.g., trunk or rear cargo area), and a cabin 120 including seats 122 disposed therein and configured to receive one or more occupants (e.g., persons). Although separate compartments 106 and 112 are illustrated, it will be appreciated that one or more of compartments 106 and 112 may be continuous with cabin 120 in various embodiments.

Vehicle 100 further includes a propulsion system 104 (e.g., an engine and/or electric motor) and wheels 106 which may be connected together through appropriate drivetrain components to facilitate motion of vehicle 100. In some embodiments, vehicle 100 may be implemented as a semi-autonomous or fully autonomous vehicle with one or more autonomous driving components 110. Vehicle 100 further includes an HVAC system 114 that may be used to cool and heat cabin 120. Vehicle 100 also includes a controller 130, an air duct 140, sensors 170, and additional components which may be used together to implement a cabin disinfection system 200 as shown in FIG. 2.

Figure 2:
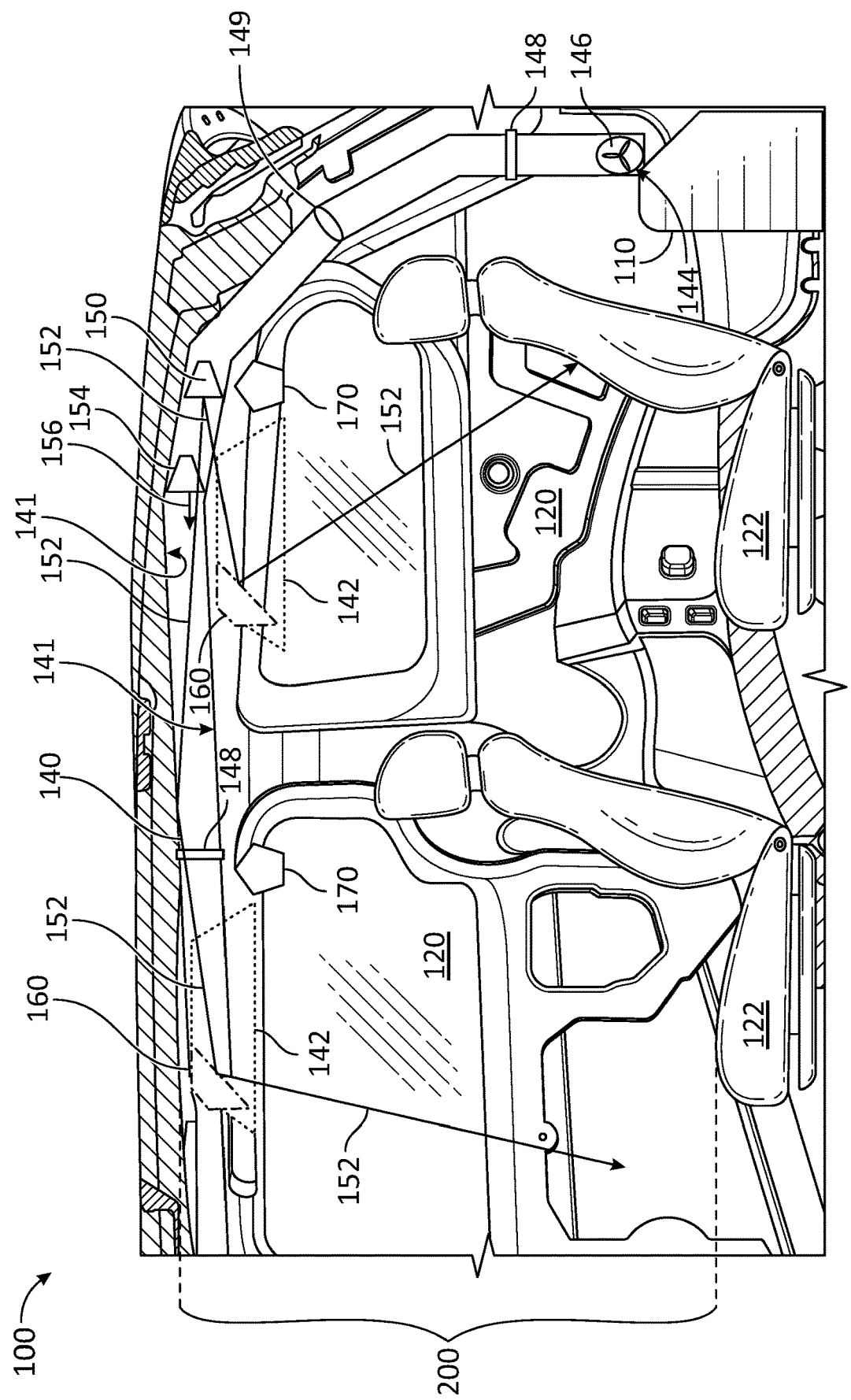
FIG. 2 illustrates an internal view of a vehicle with components of a cabin disinfection system in accordance with an embodiment of the disclosure.

In this regard, FIG. 2 illustrates an internal view of vehicle 100 with components of cabin disinfection system 200 in accordance with an embodiment of the disclosure. In some embodiments, cabin disinfection system 200 may include various components including, for example, air duct 140, ultraviolet radiation source 150, thermal infrared radiation source 154, steerable reflector systems 160, sensors 170, forced air system 146, noise cancellation system 149, filters 148, and controller 130 (shown in FIGS. 1 and 3). However, it will be understood that cabin disinfection system 200 may be implemented with greater or fewer components as appropriate in various embodiments, and that all features discussed herein are not required to be provided in all implementations. FIG. 2 further illustrates certain features of FIG. 1 in further detail including cabin 120, seats 122, and autonomous driving components 110.

As shown in FIG. 2, air duct 140 is provided with one or more inlets 142 configured to receive air particles from cabin 120 for disinfection as discussed herein. Although air duct 140 is illustrated as being positioned in a headliner area of vehicle 100, other locations are also contemplated. For example, in some embodiments, air duct 140 may be provided under a floor or in side panels of cabin 120 to receive air particles from those locations as discussed. Multiple air ducts 140 distributed among various locations may also be provided in some embodiments.

As shown, air duct 140 may extend from a front portion of cabin 120 to a rear portion of cabin 120. A forced air system 146 may be provided with air duct 140 to draw in air particles through inlets 142 and exhaust them through outlet 144 of air duct 140. As shown, outlet 144 may be positioned in proximity to autonomous driving components 110. Thus, by directing air particles from outlet 144, autonomous driving components 110 may be effectively cooled by the disinfection system. Moreover, as shown in FIG. 2, inlets 142 are located deep inside cabin 120. Accordingly, as discussed, the air particles passed by air duct 140 may be at lower temperatures than those in proximity to autonomous driving components 110, thus providing improved cooling over conventional air cooling implementations. In some embodiments, inlets 142 may be positioned substantially in the center or middle of cabin 120 in proximity to seats 122 where occupants are likely to be present. Such positioning of inlets 142 can permit air duct 140 to receive (e.g., capture) air particles in proximity to the occupants and thus prevent potential contaminants carried by the air particles from being transmitted to other portions of cabin 120.

In some embodiments, air duct 140 may be connected to HVAC system 114 as shown in FIG. 1. In this regard, disinfected air particles may be passed from air duct 140 to HVAC system 114 to provide clean air for distribution into cabin 120 by HVAC system 114.

Referring again to FIG. 2, cabin disinfection system 200 may include an ultraviolet radiation source 150 disposed in air duct 140 configured to emit corresponding ultraviolet radiation 152 at one or more selected wavelengths to neutralize various contaminants that may be carried by air particles. For example, in some embodiments, ultraviolet wavelengths in the UV-C range (e.g., 100 nm to 290 nm) may be used, however other wavelengths are also contemplated.

Air duct 140 may include internal surfaces 141 provided with reflective material configured to reflect ultraviolet wavelengths. Various types of reflective material may be used such as, for example, aluminum, mylar, glass, and/or other materials as appropriate. As a result, air duct 140 effectively operate as a waveguide to distribute the ultraviolet radiation 152 throughout the interior of air duct 140 and effectively neutralize contaminants carried by air particles therein. In some embodiments, air duct 140 itself may by implemented as a tuned physical waveguide structure with internal surfaces 141 disposed thereon to provide even more effective distribution of radiation throughout air duct 140 with minimal loss of the radiation. Additional aspects of these features are further discussed herein with regard to FIG. 4.

In FIG. 2, ultraviolet radiation 152 is illustrated with discrete ray traces. It will be understood that this is for ease of illustration and visual clarity for the reader. In this regard, it will be appreciated that the emitted ultraviolet radiation 152 may be in the form of a continuous wavefront (e.g., spherical, planar, or otherwise) and distributed over a range of angles to distribute ultraviolet radiation 152 within air duct 140.

The disinfection system may also include a thermal infrared radiation source 154 disposed in air duct 140 and configured to emit corresponding thermal infrared radiation 156 at one or more selected wavelengths to neutralize additional contaminants that may be carried by air particles. For example, in some embodiments, ultraviolet wavelengths in the long wave infrared range (e.g., 3 um to 14 um) may be used, however other wavelengths are also contemplated. In some embodiments, thermal infrared radiation 156 may be also distributed into cabin 120 in a similar manner as discussed herein with regard to ultraviolet radiation 152. Also, in FIG. 2, thermal infrared radiation 156 is illustrated with a discrete ray trace. Again, it will be understood that this is for ease of illustration and visual clarity for the reader. Accordingly, the emitted thermal infrared radiation 156 may be in the form of a continuous wavefront as similarly discussed above.

In addition to neutralizing airborne contaminants disposed in air duct 140, the disinfection system 200 may be further implemented to neutralize surface-based contaminants within cabin 120. In this regard, the disinfection system 200 may further include one or more steerable reflector systems 160 that may be used to selectively direct ultraviolet radiation 152 to various locations within cabin 120 as shown in FIG. 2. For example, in some embodiments, steerable reflector systems 160 may be configured to direct ultraviolet radiation 152 toward specific locations within cabin 120 that are detected as areas touched by occupants (e.g., high touch surfaces such as seats 122) and therefore potentially subject to surface-based contamination. Other such high touch surfaces may include, for example, door handles, seatbelts, floors, and/or other locations.

One or more sensors 170 may be provided to detect the presence of occupants within cabin 120. Sensors 170 may be implemented, for example, by cameras and/or other appropriate detectors configured to detect movement or changes in surfaces. For example, in some embodiments, sensors 170 may be implemented as cameras that monitor surfaces of cabin 120 to detect the movement of occupants or the occlusion of cabin surfaces covered with non-visible but camera-detectable coatings. In some embodiments, the sensors 170 may be configured to detect one or more disinfection events that include determining surfaces of the cabin 120 that are contaminated, an occupant has recently departed the cabin 120, an occupant is in the cabin 120, and/or the cabin 120 is unoccupied. Additionally, the sensors 170 may be configured to determine specific location or portions of the surfaces of the cabin 120 that are to be disinfected based upon detecting the presence of contaminants, high-touch surfaces, and/or a location where an occupant was seated in the cabin 120.

In addition, steerable reflector systems 160 may be configured to provide a plurality of different reflector shapes (e.g., profiles) to selectively direct ultraviolet radiation 152 into cabin 120 in various concentrated or diffuse ultraviolet radiation beam profiles into cabin 120. Additional aspects of these various surface-based disinfectant features are further discussed herein with regard to FIGS. 5 to 8.

As shown in FIG. 2, air duct 140 may further include one or more physical media filters 148 (e.g., HEPA filters or other types) as appropriate to capture additional contaminants carried by air particles. Air duct 140 may further include an active noise cancellation system 149 to reduce potential noise from being introduced into cabin 120 by the operation of forced air system 146 and/or the movement of air particles within air duct 140.

Figure 3:
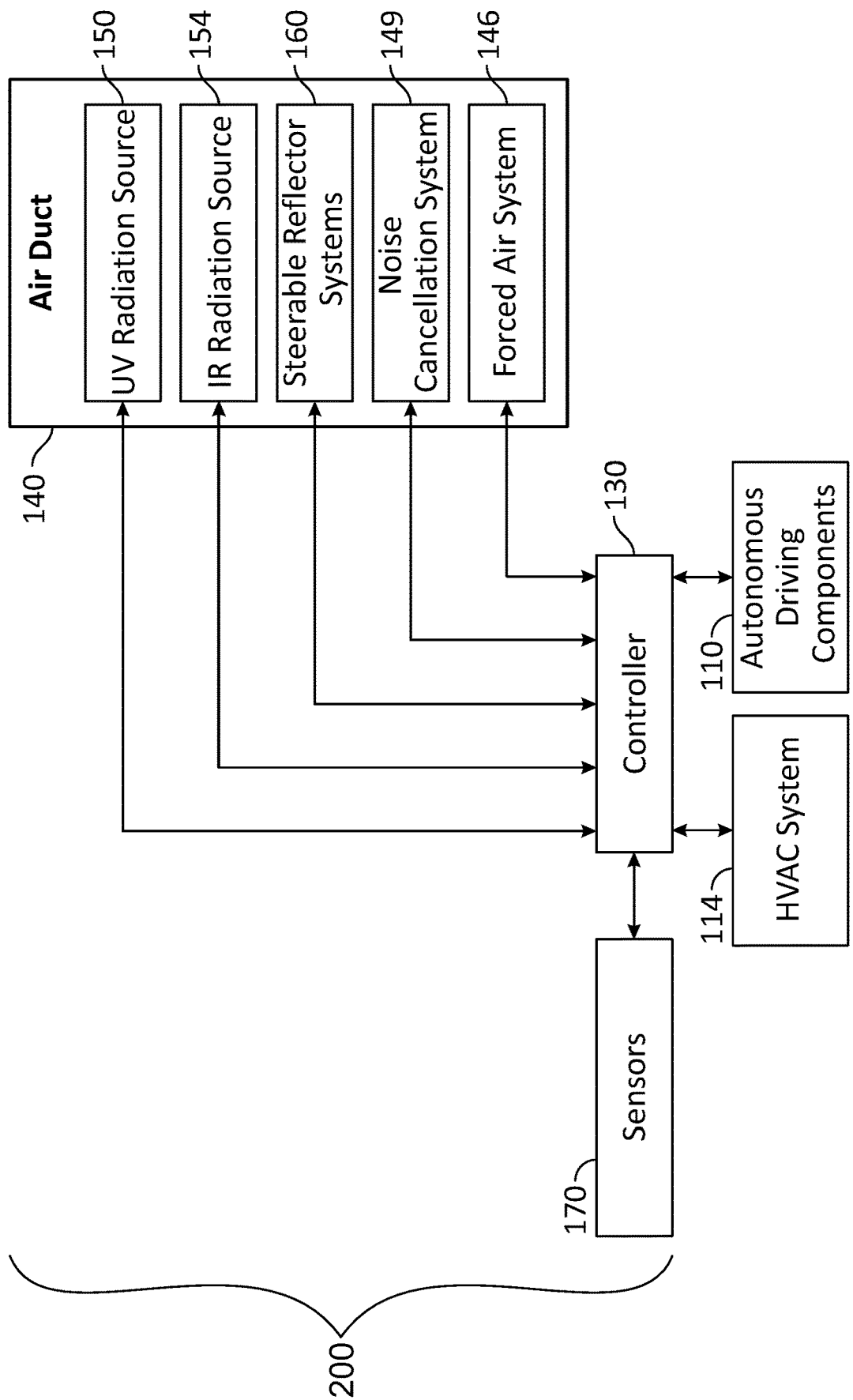
FIG. 3 illustrates a block diagram of a controller in communication with components of a cabin disinfection system in accordance with an embodiment of the disclosure.

FIG. 3 illustrates a block diagram of controller 130 in communication with various components of cabin disinfection system 200 and other components of vehicle 100 in accordance with an embodiment of the disclosure. Controller 130 may be implemented by one or more processors such as, for example, a general-purpose central processing unit (CPU), an application-specific integrated circuit (ASIC), a microcontroller, a programmable logic device (PLD), a field programmable logic device (FPGA), a digital signal processor (DSP), and/or other devices as appropriate.

Controller 130 may send and/or receive signals to the various components shown in FIG. 3 to operate cabin disinfection system 200. For example, controller 130 may selectively operate ultraviolet radiation source 150 and thermal infrared radiation source 154 at various power levels to provide desired levels of radiation for disinfection operations. Controller 130 may receive signals from sensors 170 to detect the presence of occupants and the locations of surfaces in cabin 120 touched by the occupants. Using the signals from sensors 170, controller 130 may also operate steerable reflector systems 160 to provide a selected reflector shape in the path of ultraviolet radiation 152 and direct ultraviolet radiation 152 to the touched surfaces in cabin 120. Controller 130 may further operate noise cancellation system 149 to monitor and control noise levels in cabin 120. Controller 130 may also operate forced air system 146 to provide a desired level of airflow for disinfecting air particles within air duct 140 and a desired level of cooling for autonomous driving components 110.

In some embodiments, controller 130 may further send and/or receive signals from additional components of vehicle 100. For example, controller 130 may communicate with autonomous driving components 110 (e.g., which may be implemented with appropriate processors and sensors) to monitor their temperature and/or other thermal properties and adjust the operation of forced air system 146 accordingly. In addition, controller 130 may communicate with HVAC system 114 to coordinate the passing of disinfected air particles from air duct 140 to HVAC system 114.

Although a single controller 130 is shown, it will be appreciated that any desired number of controllers 130 may be provided. For example, in some embodiments, multiple controllers 130 may be used to operate any of the various components discussed herein (e.g., ultraviolet radiation source 150 and forced air system 146 may be operated by different controllers 130 in some embodiments).

Figure 4:
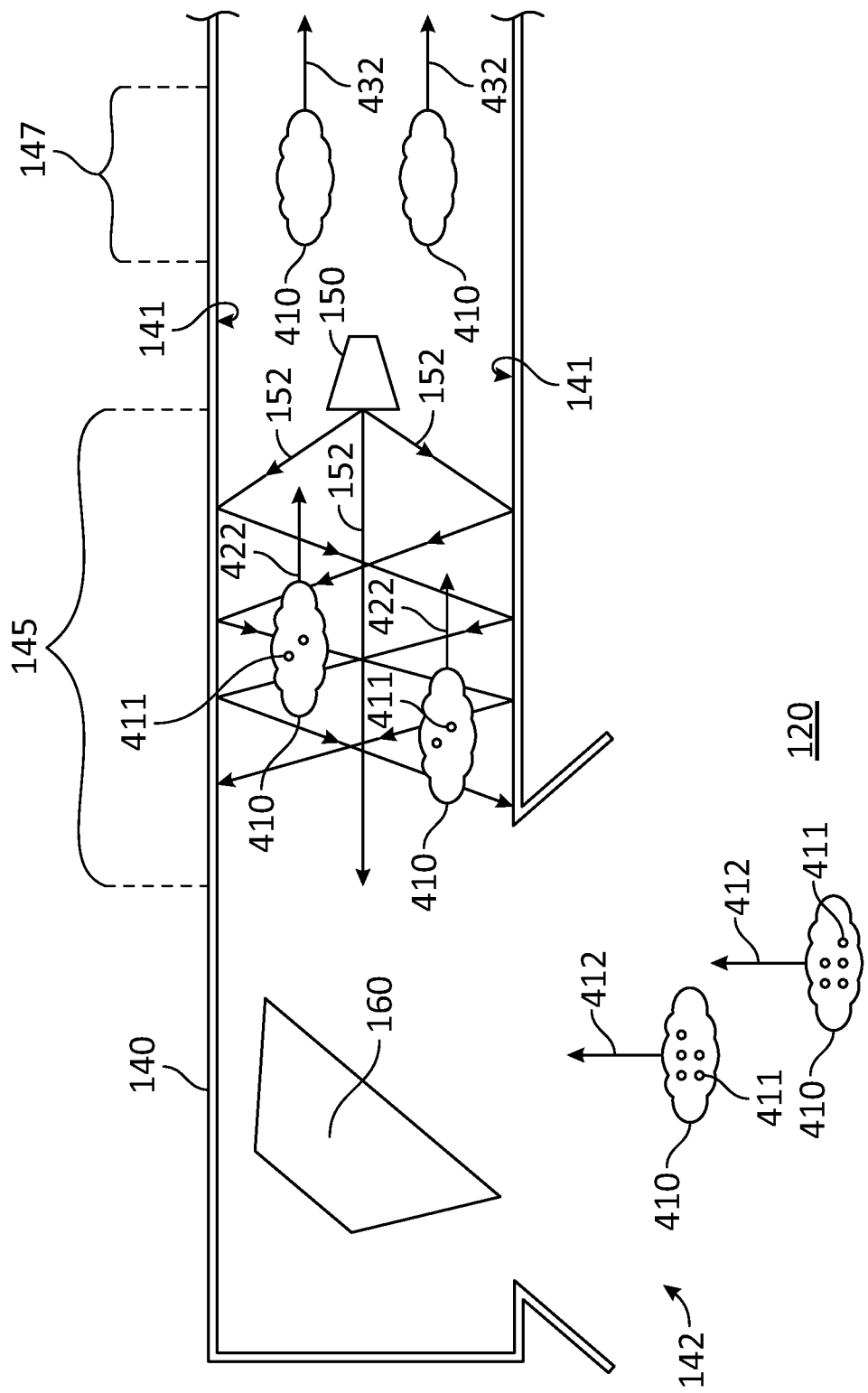
FIG. 4 illustrates an air duct of a cabin disinfection system in accordance with an embodiment of the disclosure.

FIG. 4 illustrates air duct 140 of cabin disinfection system 200 in accordance with an embodiment of the disclosure. As shown in FIG. 4, ultraviolet radiation source 150 emits ultraviolet radiation 152 into air duct 140. In FIG. 4, ultraviolet radiation 152 is illustrated with several ray traces. As discussed, this representation is provided for ease of illustration and visual clarity for the reader (e.g., ultraviolet radiation 152 may exhibit a continuous wavefront as discussed). Also, FIG. 4 illustrates ultraviolet radiation 152, it will be understood that thermal infrared radiation 156 may be used in a similar manner.

As discussed, reflective surfaces 141 cause air duct 140 to operate as a waveguide to reflect ultraviolet radiation 152 as shown. Thus, as ultraviolet radiation 152 reflects off reflective surfaces 141, it will become distributed throughout at least an interior volume 145 of air duct 140. Although interior volume 145 is illustrated as occupying a portion of air duct 140, this is shown for ease of illustration and visual clarity for the reader to demonstrate an example disinfection operation. Accordingly, it will be appreciated that, in some embodiments, ultraviolet radiation 152 may be distributed throughout the entirety of air duct 140 as appropriate.

Air particles 410 present in cabin 120 (e.g., not drawn to scale for ease of illustration) may carry various contaminants 411. The air particles 410 with their contaminants 411 are drawn in the direction of arrows 412 into inlet 142 of air duct 140 by the airflow introduced by forced air system 146 as discussed.

As air particles 410 and contaminants 411 enter the interior volume 145 of air duct 140, they receive (e.g., bombarded with) the reflected ultraviolet radiation 152 which causes the contaminants 411 carried by the air particles 410 to become neutralized. In this regard, air particles 410 are illustrated in interior volume 145 as having some contaminants 411 removed as air particles 410 undergo the process of neutralization while passing through interior volume 145.

As air particles 410 continue to travel through interior volume 145 in the direction of arrows 422, they may become fully neutralized. Accordingly, air particles 410 are illustrated at location 147 as having all contaminants 411 removed.

The decontaminated air particles 410 then continue to travel in the direction of arrows 432 as they are drawn toward outlet 144 and autonomous driving components 110 by the continued operation of forced air system 146.

FIGS. 5 to 8 illustrate various example implementations of steerable reflector systems 160 in accordance with embodiments of the disclosure. Similar to FIG. 4, ultraviolet radiation 152 is illustrated in FIGS. 5 to 8 with several ray traces. As previously discussed, this representation is provided for ease of illustration and visual clarity for the reader (e.g., ultraviolet radiation 152 may exhibit a continuous wavefront as discussed) and thermal infrared radiation 156 may be used in a similar manner as discussed for ultraviolet radiation 152.

As further discussed herein, convex and concave shapes and associated profiles illustrated in FIGS. 5 to 8 are provided in the context of optical elements implemented as reflectors with associated reflective surfaces used to reflect ultraviolet radiation 152 into cabin with associated beam profiles (e.g., convex reflective surface shapes may be used to provide diffuse profiles and concave reflective surface shapes may be used to provide concentrated profiles). As discussed, other types of optical elements may be used such as, for example, lenses. In the context of such lens-based implementations the shapes may be reversed (e.g., convex lens shapes may be used to provide concentrated profiles and concave lens shapes may be used to provide diffuse profiles).

Figure 5:
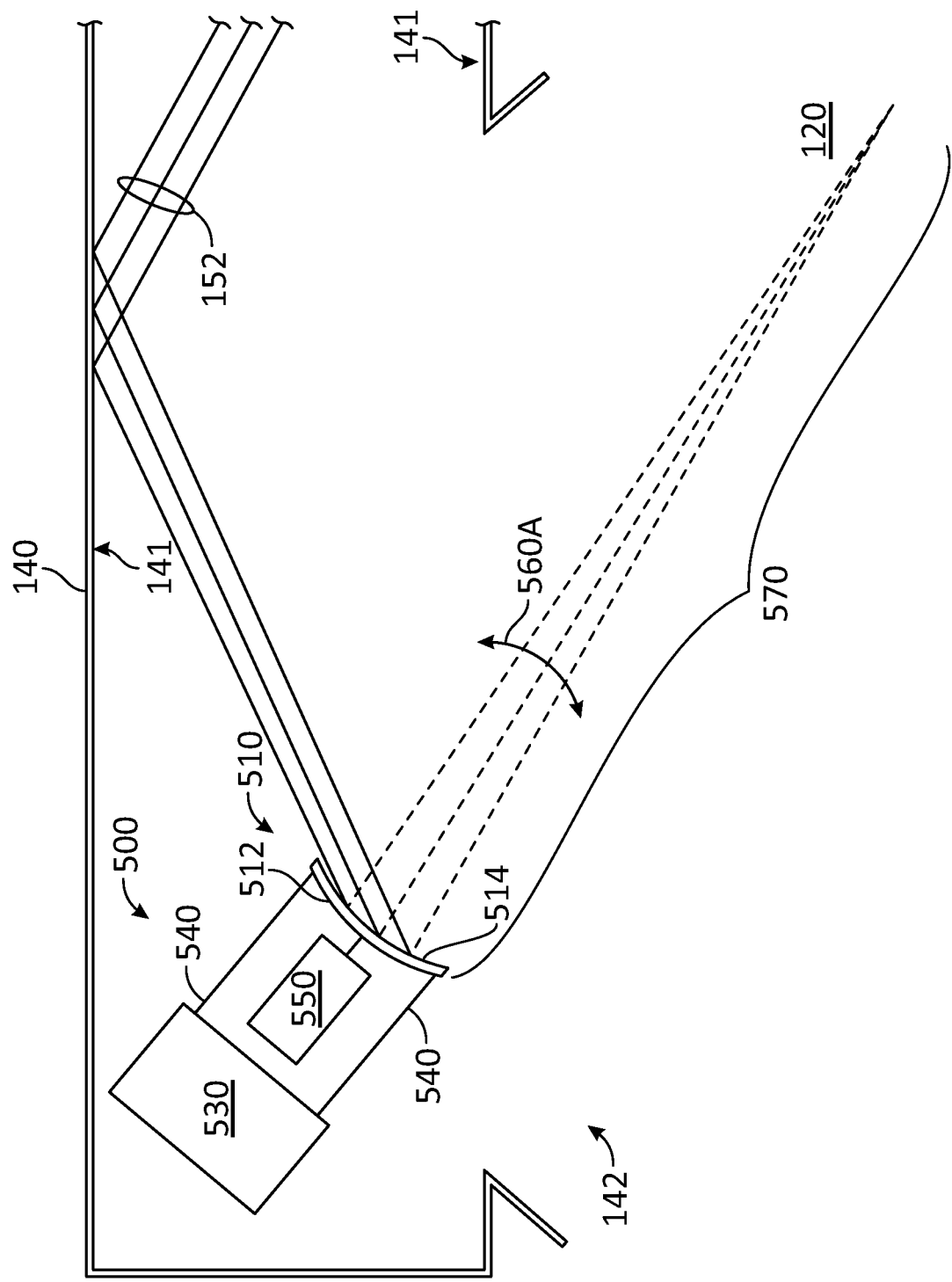
FIG. 5 illustrates a steerable reflector system having a variable reflector configured in a concave shape in accordance with an embodiment of the disclosure.
Figure 6:
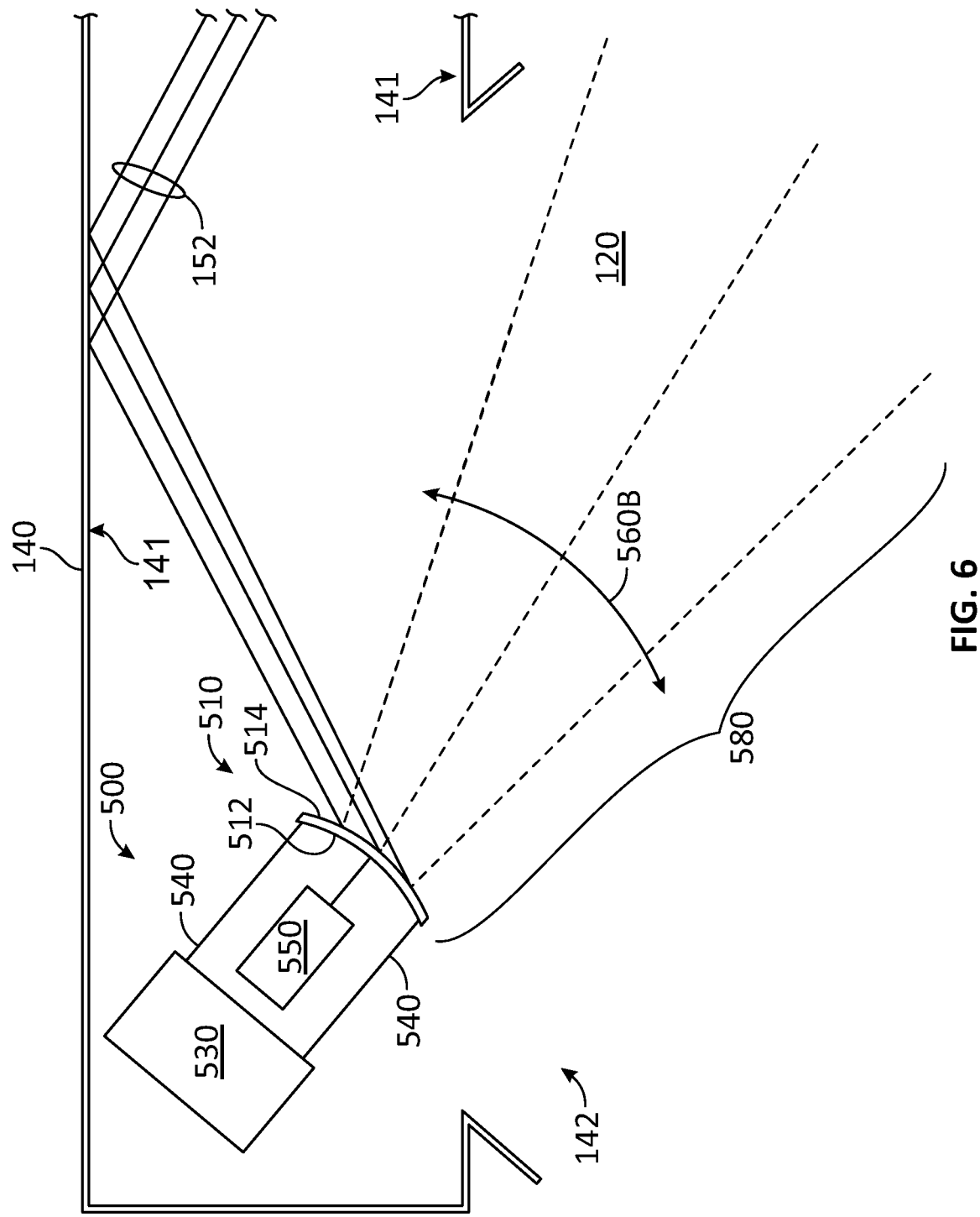
FIG. 6 illustrates a steerable reflector system having a variable reflector configured in a convex shape in accordance with an embodiment of the disclosure.

In particular, FIGS. 5 and 6 illustrate a steerable reflector system 500 having a variable reflector that may be selectively configured in convex and concave shapes (e.g., morphed between such shapes) in accordance with embodiments of the disclosure.

Reflector system 500 includes a variable shape reflector 510 having a base 512 and a reflective surface 514 disposed on base 512. Reflector system 500 further includes a shape actuator 530 connected to base 512 through adjustable linkages 540. In this regard, base 512 may be an adjustable base configured to move or flex in response to movement of linkages 540 by shape actuator 530 in response to control signals received from controller 130 (e.g., over connections shown in FIG. 3). For example, in FIG. 5, linkages 540 are illustrated in a first orientation which causes reflective surface 514 of variable reflector 510 to exhibit a concave shape.

By way of comparison, in FIG. 6, linkages 540 are illustrated in a second orientation (e.g., partially withdrawn by shape actuator 530 such that the length of linkages 540 is reduced in FIG. 6) which causes reflective surface 514 of variable reflector 510 to exhibit a convex shape.

As shown, reflector system 500 may be positioned in air duct 140 in a beam path of ultraviolet radiation 152 to reflect ultraviolet radiation 152 into cabin 120. The selective adjustment of base 512 permits variability in the shape of reflective surface 514 that receives ultraviolet radiation 152 and consequently permits ultraviolet radiation 152 to be reflected into cabin 120 in accordance with different profiles through the operation of shape actuator 530 by controller 130.

For example, in FIG. 5, the concave shape of reflective surface 514 causes ultraviolet radiation 152 to be reflected into cabin 120 in a concentrated profile 570 having a high intensity. In contrast, in FIG. 6, the convex shape of reflective surface 514 causes ultraviolet radiation 152 to be reflected into cabin 120 in a diffuse profile 580 having a lower intensity. Thus, by configuring reflective surface 514 of variable reflector 510 to exhibit different shapes (e.g., through appropriate control signals provided by controller 130 to shape actuator 530), ultraviolet radiation 152 may be selectively directed into cabin 120 with different intensities as appropriate for particular disinfection operations. For example, the concentrated profile 570 of FIG. 5 may be used to direct ultraviolet radiation 152 onto particular surfaces of cabin 120 that are known or detected to be high touch surfaces. For example, in some embodiments, sensors 170 may detect such high touch surfaces based on the presence of one or more occupants in cabin 120. Controller 130 may then select concentrated profile 570 accordingly to precisely disinfect such surfaces when the occupants are no longer present.

Conversely, the diffuse profile 580 of FIG. 6 may be used to direct ultraviolet radiation 152 more generally into cabin 120 to provide lower level disinfection at over a wider area. For example, in some embodiments, sensors 170 may detect the presence of one or more occupants and controller 130 may accordingly select diffuse profile 580 to provide low level generalized disinfection while the occupants are present.

Thus, it will be appreciated that reflector system 500 shown in FIGS. 5 and 6 provides both convex and concave shapes which may be provided, for example, by adjusting base 512 of variable reflector 510 as discussed. In some embodiments, variable reflector 510 may be reversible by shape actuator 530 with convex and concave shapes provided on opposite sides.

Reflector system 500 also includes a steering actuator 550 which may be used to adjust the orientation of reflector 510 in relation to the received ultraviolet radiation 152 to steer the concentrated profile 570 or the diffuse profile 580 through a range of orientations (e.g., denoted by arrows 560A in FIG. 5 and arrows 560B in FIG. 6) to direct the reflected ultraviolet radiation 152 to desired locations within cabin 120. In various embodiments, steering actuator 550 may operate in one or more dimensions to precisely orient reflector 510 as desired for particular applications.

Figure 7:
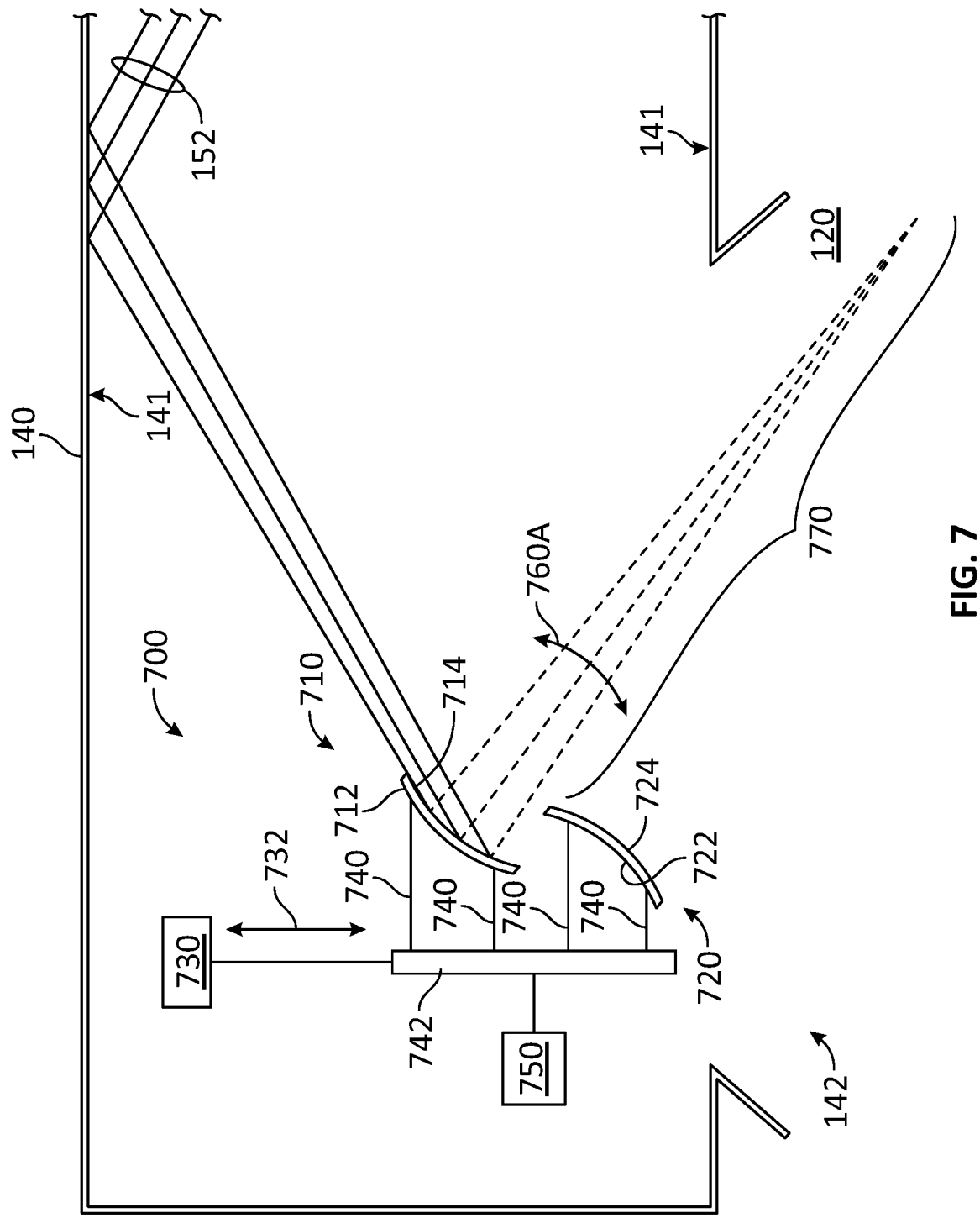
FIG. 7 illustrates a steerable reflector system having fixed reflectors with a concave reflector in operation in accordance with an embodiment of the disclosure.
Figure 8:
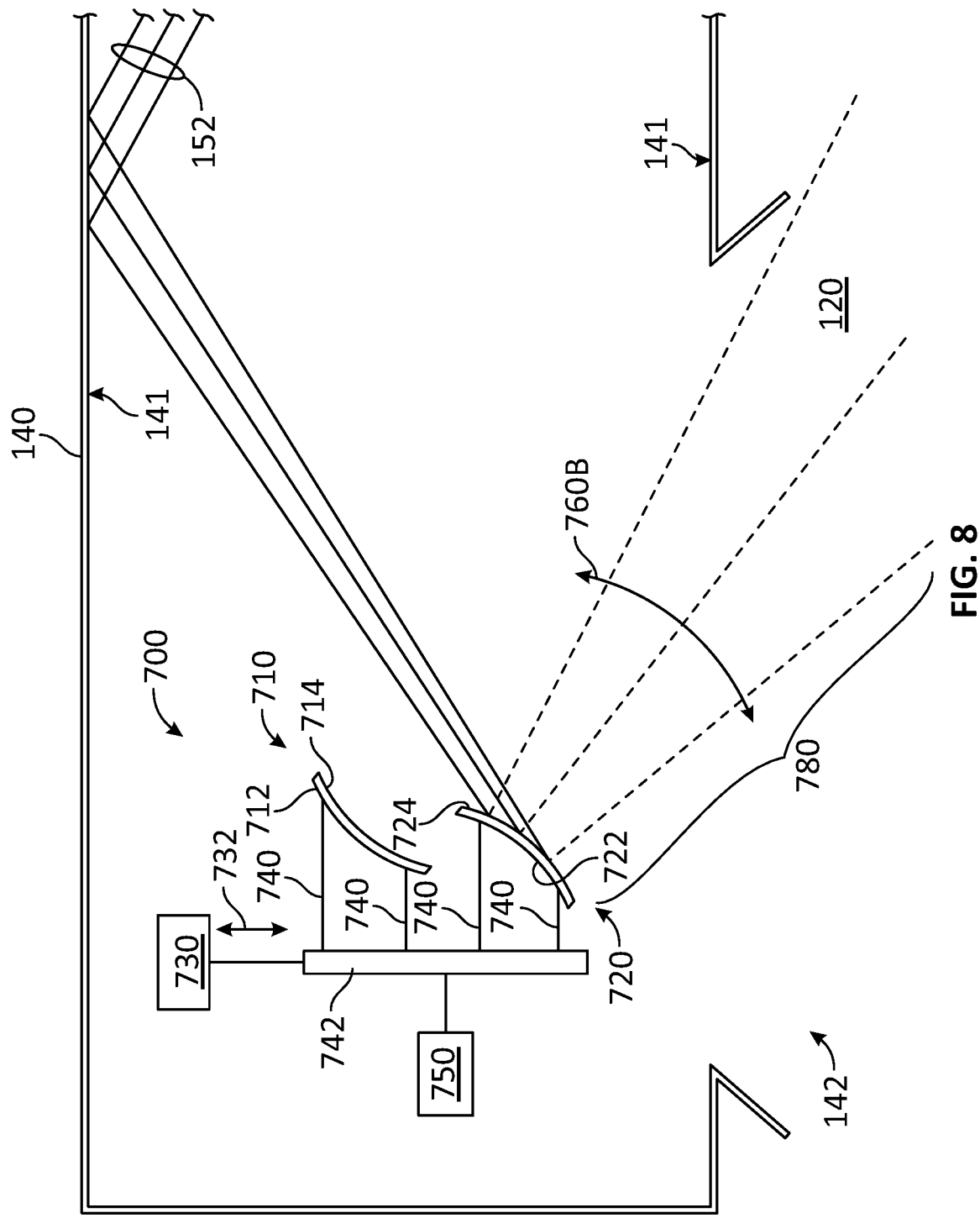
FIG. 8 illustrates a steerable reflector system having fixed reflectors with a convex reflector in operation in accordance with an embodiment of the disclosure.

FIGS. 7 and 8 illustrate a steerable reflector system 700 having separate reflectors with fixed convex and concave shapes in accordance with embodiments of the disclosure. Reflector system 700 includes a fixed shape reflector 710 having a base 712 and a reflective surface 714 disposed on base 712 in a fixed concave shape. Reflector system 700 also includes a fixed shape reflector 720 having a base 722 and a reflective surface 724 disposed on base 722 in a fixed convex shape. Reflectors 710 and 720 may be connected to a mount 742 through linkages 740 as shown. In some embodiments, linkages 740 may be fixed in order to position reflectors 710 and 720 in a fixed orientation relative to mount 742. In other embodiments, linkages 740 may be adjustable to permit adjustment of the orientation of reflectors 710 and 720 relative to mount (e.g., to adjust their associated reflected beam angles).

Reflector system 700 further includes a translation actuator 730 configured to selectively adjust the position of reflectors 710 and 720 relative to ultraviolet radiation 152 by selectively translating mount 742 in the directions of arrows 732 in response to control signals received from controller 130. As a result, reflector 710 (e.g., having a concave shape) and reflector 720 (e.g., having a convex shape) may be selectively positioned to reflect ultraviolet radiation 152 into cabin 120.

For example, in FIG. 7, the concave shape of reflective surface 714 of reflector 710 is positioned to receive ultraviolet radiation 152 which causes ultraviolet radiation 152 to be reflected into cabin 120 in a concentrated profile 770 having a high intensity as similarly discussed with regard to FIG. 5. In contrast, in FIG. 8, the convex shape of reflective surface 724 of reflector 720 is positioned to receive ultraviolet radiation 152 which causes ultraviolet radiation 152 to be reflected into cabin 120 in a diffuse profile 780 having a lower intensity as similarly discussed with regard to FIG. 6.

As similarly discussed with regard to FIGS. 5 and 6, in some embodiments, sensors 170 may detect high touch surfaces based on the presence of one or more occupants in cabin 120. Controller 130 may then select concentrated profile 770 accordingly to precisely disinfect such surfaces when the occupants are no longer present. In some embodiments, sensors 170 may detect the presence of one or more occupants and controller 130 may accordingly select diffuse profile 780 to provide low level generalized disinfection while the occupants are present.

Reflector system 700 also includes a steering actuator 750 which may be used to adjust the orientation of reflectors 710 and 720 in relation to the received ultraviolet radiation 152 to steer the concentrated profile 770 or the diffuse profile 780 through a range of orientations (e.g., denoted by arrows 760A in FIG. 7 and arrows 760B in FIG. 8) to direct the reflected ultraviolet radiation 152 to desired locations within cabin 120 and in one or more dimensions as similarly discussed with regard to FIGS. 5 and 6.

Figure 9:
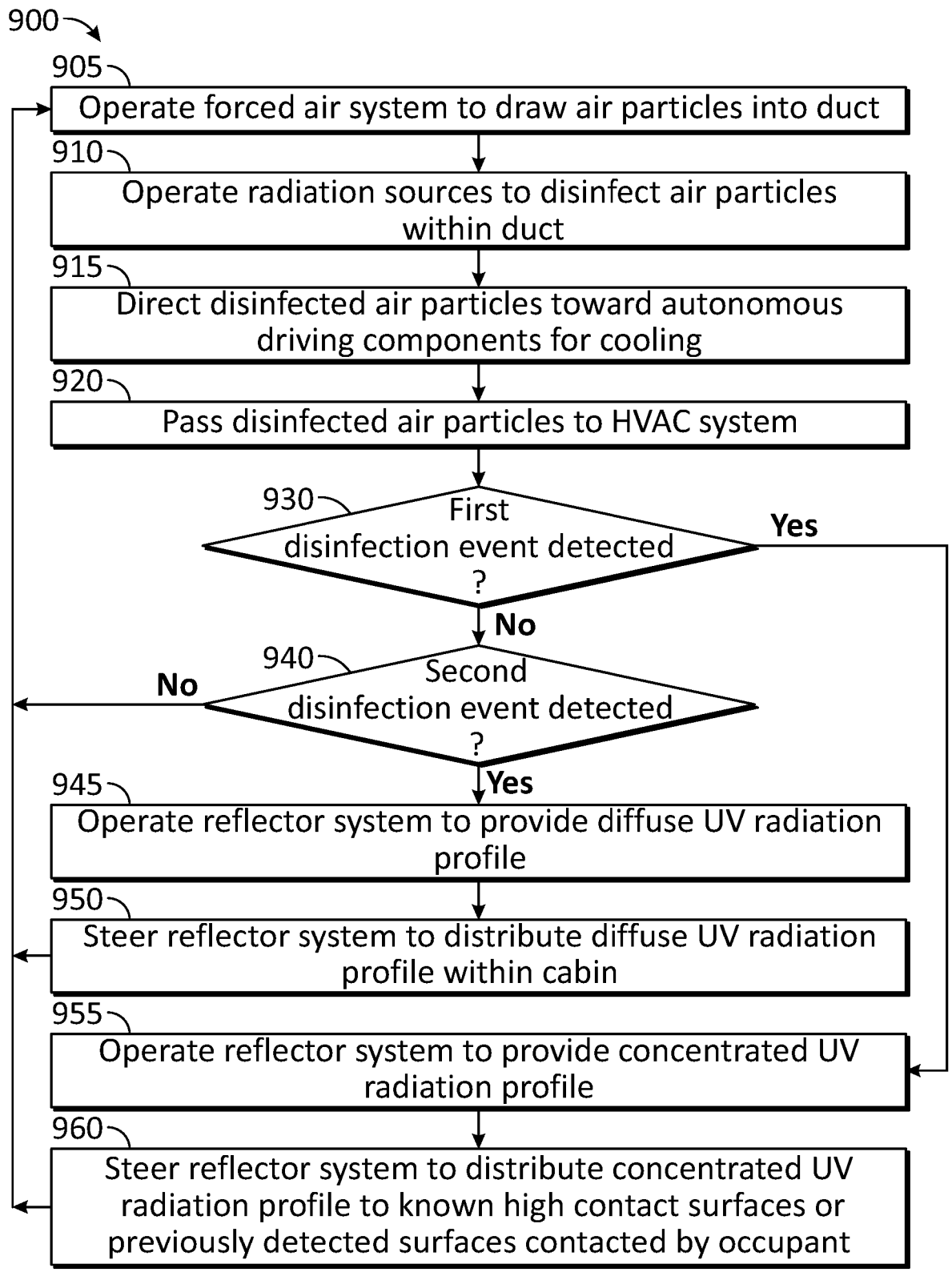
FIG. 9 illustrates a flow diagram of a process of operating a cabin disinfection system in accordance with an embodiment of the disclosure.

FIG. 9 illustrates a flow diagram of a process 900 of operating cabin disinfection system 200 in accordance with an embodiment of the disclosure. The process 900 of FIG. 9 is illustrative only and may have greater or fewer operations in various embodiments as appropriate.

In block 905, controller 130 operates forced air system 146 to draw air particles 410 into air duct 140. In block 910, controller 130 operates ultraviolet radiation source 150 and optionally operates thermal infrared radiation source 154 to disinfect air particles 410 within air duct 140 as discussed.

In block 915, the continued operation of forced air system 146 directs the disinfected air particles 410 through outlet 144 toward autonomous driving components 110 to provide air cooling as discussed. In block 920, the disinfected air particles 410 are optionally passed by air duct 140 to HVAC system 114 for potential recirculation into cabin 120.

In block 930, the sensors 170 may determine whether a first disinfection event is present in the cabin. In some examples, the first disinfection event includes the sensors 170 determining the presence of contaminants on one or more surfaces of the cabin 120. In some examples, the first disinfection event includes the sensors 170 determining that an amount of a contaminant in the cabin 120 is equal to or greater than a threshold amount. In some embodiments, the controller 130 may not operate the radiation source if an occupant is detected in the cabin 120. If yes, at block 930, then the process continues to block 955. If no, at block 930, then the process continues to block 940.

In block 940, controller 130 determines whether to disinfect cabin 120 in accordance with a presence of a second disinfection event. According to some examples, the second disinfection event may include a general presence of a contaminant in various regions throughout the cabin 120. According to some examples, the second disinfection event may include an amount of a contaminant in the cabin 122 that is less than a threshold amount. In some embodiments, the controller 130 may not operate the radiation source if an occupant is detected in the cabin 120. If no, at block 940, then the process returns to block 905. If yes, at block 940, the process continues to block 945.

In block 945, controller 130 operates one or more steerable reflector systems 160 to direct ultraviolet radiation 152 into cabin 120 with a diffuse profile to provide low intensity disinfection of cabin 120 in accordance with the second disinfection event. For example, in various embodiments, controller 130 may operate shape actuator 530 to configure reflector 510 with a convex shape to provide diffuse profile 580 as shown in FIG. 6 or may operate translation actuator 630 to position fixed convex reflector 720 to provide diffuse profile 780 as shown in FIG. 8. Also in block 945, in some embodiments, controller 130 may adjust an intensity of ultraviolet radiation source 154 to a low intensity level while the detected occupant is present (e.g., to restrict the amount of ultraviolet radiation emitted into cabin 120).

In block 950, controller 130 operates steering actuator 550 or 750 to direct the diffuse profile 580 or 780 to desired locations of cabin 120 for decontamination. The process 900 then returns to block 905.

Referring again to block 930, if no occupant is detected, then the process continues to block 955 where a high intensity disinfection of cabin 120 may be performed. In block 955, controller 130 operates reflector system 160 to direct ultraviolet radiation 152 into cabin 120 with a concentrated profile to provide high intensity disinfection of cabin 120. For example, in various embodiments, controller 130 may operate shape actuator 530 to configure reflector 510 with a concave shape to provide concentrated profile 570 as shown in FIG. 5 or may operate translation actuator 730 to position fixed concave reflector 710 to provide concentrated profile 770 as shown in FIG. 7. Also in block 955, in some embodiments, controller 130 may adjust an intensity of ultraviolet radiation source 154 to a high intensity level while no occupant is detected (e.g., to emit higher levels of ultraviolet radiation into cabin 120 for high intensity disinfection while not occupant is present).

In block 950, controller 130 operates steering actuator 550 or 650 to direct the concentrated profile 570 or 670 to desired locations of cabin 120 for decontamination. The process 900 then returns to block 905.

In view of the present disclosure, it will be appreciated that a vehicle cabin disinfection system and related methods have been provided that may neutralize airborne and surface-based contaminants in a comprehensive manner. In addition, such implementations may be integrated with a forced air cooling system used to cool autonomous driving components, thus providing an efficient and effective disinfection solution for a semi-autonomous or fully autonomous vehicles.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as program code and/or data, can be stored on one or more computer readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the present invention. Accordingly, the scope of the invention is defined only by the following claims.

What is claimed is:

1. A disinfection system for a cabin of a vehicle, the disinfection system comprising:
    a controller;
    an ultraviolet radiation source in communication with the controller and configured to emit ultraviolet radiation;
    an air duct defined by an inlet and an outlet, the ultraviolet radiation source disposed within the air duct, the inlet configured to receive air particles from within the cabin of the vehicle, the air duct comprising one or more internal reflective surfaces configured to reflect the ultraviolet radiation so as to disinfect the air particles within the air duct and transmit the disinfected air particles out of the air duct via the outlet; and a steerable optical system coupled to the air duct, the steerable optical system configured to receive the ultraviolet radiation and selectively direct the ultraviolet radiation to disinfect the cabin.

2. The system of claim 1, wherein the steerable optical system comprises:
an actuator in communication with the controller;
a variable optical element, wherein the controller is configured to operate the actuator to adjust the variable optical element to transition between:
a first shape to direct the ultraviolet radiation into the cabin in a diffuse profile having a first intensity; and
a second shape to direct the ultraviolet radiation into the cabin in a concentrated profile having a second intensity greater than the first intensity.

3. The system of claim 2, further comprising:
a sensor configured to detect a presence of a disinfection event in the cabin of the vehicle; and
wherein the controller is configured to operate the actuator to adjust the variable optical element in response to the detection of the presence of the disinfection event to transition the variable optical element between the first shape and the second shape.

4. The system of claim 1, wherein the steerable optical system comprises:
a first optical element having a fixed first shape configured to direct the ultraviolet radiation into the cabin in a diffuse profile having a first intensity;
a second optical element having a fixed second shape configured to direct the ultraviolet radiation into the cabin in a concentrated profile having a second intensity greater than the first intensity; and
an actuator in communication with the controller to selectively position the first and second optical elements in a beam path of the ultraviolet radiation source to direct the ultraviolet radiation into the cabin in the diffuse profile and the concentrated profile, respectively.

5. The system of claim 3, wherein the disinfection event includes at least one of:
the sensor detecting that an occupant has recently departed the cabin;
the sensor detecting a presence of a contaminant in the cabin; or
the sensor detecting that the cabin is unoccupied.

6. The system of claim 1, further comprising an actuator in communication with the controller to steer the steerable optical system to direct the ultraviolet radiation toward one or more surfaces of the cabin.

7. The system of claim 6, further comprising a sensor configured to determine portions of the one or more surfaces of the cabin that are to be disinfected, wherein the controller is configured to operate the actuator to direct the ultraviolet radiation toward one or more portions of the surfaces that are to be disinfected.

8. The system of claim 1, wherein the ultraviolet radiation source is a first radiation source, the system further comprising a second radiation source disposed within the air duct and configured to emit thermal infrared radiation, wherein the one or more internal reflective surfaces of the air duct are configured to reflect the thermal infrared radiation so as to disinfect the air particles within the air duct.

9. The system of claim 1, further comprising a forced air system to direct the disinfected air particles from the outlet of the air duct toward an autonomous driving component of the vehicle to cool the autonomous driving component, wherein the air duct is further connected to a Heating Ventilation and Air Conditioning (HVAC) system of the vehicle and configured to pass the disinfected air particles to the HVAC system.

10. A method of performing a disinfection process for a cabin of a vehicle, the cabin including an air duct, the method comprising, by a controller:
receiving, from a sensor in communication with the controller, an indication of one or more surfaces of the cabin that are to undergo the disinfection process;
adjusting an orientation of a steerable optical system coupled to the air duct based on the indication of the one or more surfaces of the cabin that are to undergo the disinfection process; and
while the steerable optical system is in the adjusted orientation, causing an ultraviolet radiation source in communication with the controller to direct ultraviolet radiation to the steerable optical system, wherein the ultraviolet radiation source is disposed within the air duct, and the air duct includes one or more internal reflective surfaces that reflect the ultraviolet radiation towards the steerable optical system such that the steerable optical system selectively directs the ultraviolet radiation to the one or more surfaces of the cabin.

11. The method of claim 10, wherein the steerable optical system comprises an actuator and a variable optical element, and the method further comprises:
controlling the actuator to adjust the variable optical element to transition between:
a first shape such as to direct the ultraviolet radiation in a diffuse profile having a first intensity into the cabin; and
a second shape such as to direct the ultraviolet radiation in a concentrated profile having a second intensity greater than the first intensity into the cabin.

12. The method of claim 11, wherein the one or more surfaces of the cabin are determined by the sensor to undergo the disinfection process based upon at least one event:
the sensor detecting that an occupant has recently departed the cabin;
the sensor detecting a presence of a contaminant in the cabin; or
the sensor detecting that the cabin is unoccupied.

13. The method of claim 12, further comprising:
adjusting an intensity of the ultraviolet radiation that is directed to the one or more surfaces of the cabin in accordance with the at least one event by transitioning the variable optical element between the first shape and the second shape.

14. The method of claim 10, wherein the steerable optical system comprises an actuator, a first optical element having a fixed first shape, and a second optical element having a fixed second shape, the adjusting orientation of the steerable optical system comprises controlling the actuator to selectively position the first and second optical elements in a beam path of the ultraviolet radiation source to direct the ultraviolet radiation into the cabin in a diffuse profile having a first intensity and in a concentrated profile having a second intensity greater than the first intensity, respectively.

15. The method of claim 10, wherein an inlet of the air duct is configured to receive air particles from within the cabin of the vehicle, and the one or more internal reflective surfaces reflect the ultraviolet radiation so as to disinfect the air particles within the air duct and, an outlet of the air duct transmits the disinfected air particles out of the air duct via the outlet.

16. The method of claim 15, wherein the ultraviolet radiation source is a first radiation source, the method further comprising:
controlling a second radiation source disposed within the air duct to emit thermal infrared radiation such that the one or more internal reflective surfaces of the air duct reflect the thermal infrared radiation so as to disinfect the air particles within the air duct.

17. The method of claim 15, further comprising:
controlling a forced air system to direct the disinfected air particles from the outlet of the air duct toward an autonomous driving component of the vehicle to cool the autonomous driving component, wherein the air duct is further connected to a Heating Ventilation and Air Conditioning (HVAC) system of the vehicle and configured to pass the disinfected air particles to the HVAC system.

18. A disinfection system for a cabin of a vehicle, the disinfection system comprising:
a controller;
an ultraviolet radiation source in communication with the controller and configured to emit ultraviolet radiation;
an air duct defined by an inlet and an outlet, the ultraviolet radiation source disposed within the air duct, wherein the air duct includes one or more internal reflective surfaces configured to reflect the ultraviolet radiation emitted by the ultraviolet radiation source;
a sensor in communication with the controller, the sensor configured to (i) determine a presence of a disinfection event in the cabin, and (ii) provide an indication to the controller of one or more surfaces of the cabin that are to be disinfected in association with the disinfection event; and
a steerable optical system including one or more optical elements coupled to the air duct, the one or more optical elements configured to transition between a first shape and a second shape, the steerable optical system configured to (i) transition from the first shape to the second shape, and (ii) receive the ultraviolet radiation and selectively direct the ultraviolet radiation by the one or more optical elements while in the second shape to disinfect the one or more surfaces of the cabin.

19. The system of claim 18, wherein the inlet is configured to receive air particles from within the cabin of the vehicle, and the one or more internal reflective surfaces are configured to reflect the ultraviolet radiation so as to disinfect the air particles within the air duct and transmit the disinfected air particles out of the air duct via the outlet.

20. The system of claim 18, wherein the disinfection event includes at least one of:
the sensor detecting that an occupant has recently departed the cabin;
the sensor detecting a presence of a contaminant in the cabin; or
the sensor detecting that the cabin is unoccupied.

* * * * *